United States Patent [19]
Beeley et al.

[11] Patent Number: 6,087,334
[45] Date of Patent: Jul. 11, 2000

[54] ANTI-DIABETIC PEPTIDES

[75] Inventors: Nigel Robert Arnold Beeley, Solana Beach; Kathryn S. Prickett, San Diego, both of Calif.

[73] Assignee: Amylin Pharmaceuticals, Inc., San Diego, Calif.

[21] Appl. No.: 09/138,056

[22] Filed: Aug. 21, 1998

[51] Int. Cl.[7] .......................... A61K 38/00; A61K 39/00; C07K 5/00; C07K 7/00
[52] U.S. Cl. ............................. 514/13; 514/2; 530/300; 530/308; 530/326; 424/184.1; 424/185.1
[58] Field of Search ................................. 530/300, 308, 530/326; 514/2, 13; 424/184.1, 185.1

[56] References Cited

U.S. PATENT DOCUMENTS

| | | | |
|---|---|---|---|
| 5,384,250 | 1/1995 | Murgita | 435/69.6 |
| 5,814,600 | 9/1998 | Rink et al. | 514/4 |
| 5,965,528 | 10/1999 | Murgita | 514/12 |

*Primary Examiner*—Avis M. Davenport
*Attorney, Agent, or Firm*—Lyon & Lyon LLP

[57] ABSTRACT

Compounds of formula I which act as amylin agonists with respect to certain desired amylin activities and as calcitonin agonists with respect to certain desired calcitonin activities are provided. Such compounds are useful in treating disturbances in fuel metabolism in mammals, including, but not limited to diabetes mellitus, including Type I diabetes and Type II diabetes. The present invention also relates to methods of treating Type I diabetes, treating Type II diabetes and to methods of beneficially regulating gastrointestinal motility comprising administration of a therapeutically effective among of one of the compounds. Also provided are pharmaceutical composition comprising a compound of formula I and a pharmaceutically acceptable carrier.

82 Claims, No Drawings

ANTI-DIABETIC PEPTIDES

FIELD OF THE INVENTION

The present invention is directed to novel peptide compounds for use as calcitonin agonists and as amylin agonists with respect to certain desired amylin activities. These compounds are useful in treating disturbances in fuel metabolism in mammals, including, but not limited to diabetes mellitus, including Type I diabetes and Type II diabetes.

BACKGROUND AND INTRODUCTION TO THE INVENTION

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type I (insulin-dependent diabetes mellitus or IDDM) and Type II (non-insulin dependent diabetes mellitus or NIDDM) diabetes. The hyperglycemia present in individuals with Type I diabetes is associated with deficient, reduced, or nonexistent levels of insulin which are insufficient to maintain blood glucose levels within the physiological range. Treatment of Type I diabetes involves administration of replacement doses of insulin, generally by a parental route. The hyperglycemia present in individuals with Type II diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β cells which are responsible for the secretion of insulin. Thus, initial therapy of Type II diabetes may be based on diet and lifestyle changes augmented by therapy with oral hypoglycemic agents such as sulfonylureas. Insulin therapy is often required, however, especially in the latter states of the disease, in attempting to produce some control of hyperglycemia and minimize complications of the disease.

The structure and biology of amylin have previously been reviewed. See, for example, Young, *Current Opinion in Endocrinology and Diabetes*, 4:282–290 (1997); Gaeta and Rink, *Med. Chem. Res.*, 3:483–490 (1994); and, Pittner et al., *J. Cell. Biochem.*, 55S:19–28 (1994). Amylin is a 37 amino acid peptide hormone. It was isolated, purified and chemically characterized as the major component of amyloid deposits in the islets of pancreases of deceased human Type II diabetics (Cooper et al., *Proc. Natl. Acad. Sci. USA*, 84:8628–8632 (1987)). The amylin molecule has two important post-translational modifications: the C-terminus is amidated, i.e., the 37th residue is tyrosinamide, and the cysteines in positions 2 and 7 are cross-linked to form an intra-molecular N-terminal loop, both of which are essential for full biologic activity (Cooper et al., *Proc. Natl. Acad. Sci. USA*, 85:7763–7766 (1988)). Amylin is the subject of U.S. Pat. No. 5,367,052, issued Nov. 22, 1994, in the names of Garth Cooper and Antony Willis, who discovered the hormone.

In Type I diabetes and late stage Type II diabetes, amylin has been shown to be deficient and combined replacement with insulin has been proposed as a preferred treatment over insulin alone in all forms of insulin-dependent diabetes. The use of amylin and amylin agonists for the treatment of diabetes mellitus is the subject of U.S. Pat. No. 5,175,145, issued Dec. 29, 1992. Pharmaceutical compositions containing amylin and amylin plus insulin are described in U.S. Pat. No. 5,124,314, issued Jun. 23, 1992.

Excess amylin action has been said to mimic key features of the earlier stages of Type II diabetes and amylin blockade has been proposed as a novel therapeutic strategy. It has been disclosed in U.S. Pat. No. 5,266,561, issued Nov. 30, 1993, that amylin causes reduction in both basal and insulin-stimulated incorporation of labeled glucose into glycogen in skeletal muscle. The treatment of Type II diabetes and insulin resistance with amylin antagonists is disclosed.

Amylin is primarily synthesized in pancreatic beta cells and is secreted in response to nutrient stimuli such as glucose and arginine. Studies with cloned beta-cell tumor lines (Moore et al., *Biochem. Biophys. Res. Commun.*, 179(1) (1991)) and perfused rat pancreases (Ogawa et al., *J. Clin. Invest.*, 85:973–976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with acute stimuli in any one preparation. However, during prolonged stimulation by elevated glucose, the amylin:insulin ratio can progressively increase (Gedulin et al., *Biochem. Biophys. Res. Commun.*, 180(1):782–789 (1991)). Thus, amylin and insulin are not always secreted in a constant ratio.

It has been discovered and reported that certain actions of amylin are similar to non-metabolic actions of CGRP and calcitonin; however, the metabolic actions of amylin discovered during investigations of this recently identified protein appear to reflect its primary biological role. At least some of these metabolic actions are mimicked by CGRP, albeit at doses which are markedly vasodilatory (see, e.g., Leighton and Cooper, *Nature*, 335:632–635 (1988)); Molina et al., *Diabetes*, 39:260–265 (1990)).

It is believed that amylin acts through receptors present in plasma membranes. Studies of amylin and CGRP, and the effect of selective antagonists, have led to reports that amylin acts via its own receptor (Beaumont et al., *Br. J. Pharmacol.*, 115(5):713–715 (1995); Wang et al., *FEBS Letts.*, 219:195–198 (1991 b)), in contrast to the conclusion of other workers that amylin may act primarily at CGRP receptors (e.g, Chantry et al., *Biochem. J.*, 277:139–143 (1991)); Zhu et al., *Biochem. Biophys. Res. Commun.*, 177(2):771–776 (1991)). Amylin receptors and their use in methods for screening and assaying for amylin agonist and antagonist compounds are described in U.S. Pat. No. 5,264, 372, issued Nov. 23, 1993.

Amylin and amylin agonists have also been shown to suppress glucagon secretion. When influences that would otherwise affect glucagon secretion were controlled (plasma glucose, insulin and blood pressure), amylin reportedly suppressed the glucagon response to arginine in rats. Gedulin et al., *Metabolism*, 46:67–70 (1997). The amylin anaogue, pramlintide ($^{25,28,29}$Pro-human amylin), has been reported to eliminate the post-prandial surge in glucagon concentration in subjects with Type I diabetes (Fineman et al., *Diabetes*, 40:30A (1997)). Pramlintide, and other amylin agonist analogues, are described and claimed in U.S. Pat. No. 5,686,411, issued Nov. 11, 1997.

Amylin and amylin agonists potently inhibit gastric emptying in rats (Young et al., *Diabetologia* 38(6):642–648 (1995)), dogs (Brown et al., *Diabetes* 43(Suppl 1):172A (1994)) and humans (Macdonald et al., *Diabetologia* 38(Suppl 1):A32 (abstract 118)(1995)). Gastric emptying is reportedly accelerated in amylin-deficient Type I diabetic BB rats (Young et al., *Diabetologia*, supra; Nowak et al., *J. Lab. Clin. Med.*, 123(1):110–6 (1994)) and in rats treated with the amylin antagonist, AC187 (Gedulin et al., *Diabetologia*, 38(Suppl 1):A244 (1995). The effect of amylin on gastric emptying appears to be physiological (operative at concentrations that normally circulate).

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.*, 183:2221 (1990); Wang et al., *FEBS Letts.*, 291:195–198 (1991)).

Injected into the brain, or administered peripherally, amylin has been reported to suppress food intake, e.g., Chance et al., *Brain Res.*, 539:352–354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease (see, e.g., Zaidi et al., *Trends in Endocrinal. and Metab.*, 4:255–259 (1993). From the available data, amylin appears to be 10 to 30 times less potent than human calcitonin for these actions. Interestingly, it was reported that amylin increased osteoclast cAMP production but not cytosolic $Ca^{2+}$, while calcitonin does both (Alam et al., *Biochem. Biophys. Res. Commun.*, 179(1):134–139 (1991)). It was suggested, though not established, that amylin may act via a single receptor type whereas calcitonin may act via two receptors, one of which may be common to amylin activity.

It has also been discovered that, surprisingly in view of its previously described renal vasodilator and other properties, amylin markedly increases plasma renin activity in intact rats when given subcutaneously in a manner that avoids any disturbance of blood pressure. This latter point is important because lowered blood pressure is a strong stimulus to renin release. Amylin antagonists, such as amylin receptor antagonists, including those selective for amylin receptors compared to CGRP and/or calcitonin receptors, can be used to block the amylin-evoked rise of plasma renin activity. The use of amylin antagonists to treat renin-related disorders is described in U.S. Pat. No. 5,376,638, issued Dec. 27, 1994.

In normal humans, fasting amylin levels from 1 to 10 pM and post-prandial or post-glucose levels of 5 to 20 pM have been reported (see, e.g., Koda et al., *The Lancet*, 339:1179–1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3- to 4-fold higher levels in insulin-resistant people. In Type I diabetes, where beta cells are destroyed, amylin levels are at or below the levels of detection and do not rise in response to glucose (Koda et al., *The Lancet*, 339:1179–1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension*, 19:I-101–I-109 (1991)).

In mammals, calcitonin functions in the regulation of bone marrow turnover and calcium metabolism. Calcitonin, which is caused to be released from the thyroid by elevated serum calcium levels, produces actions on bone and other organs which tend to reduce serum calcium levels. Calcitonin inhibits osteoclast activity and reduces bone resorption, thereby reducing serum calcium levels. Calcitonin also alters calcium, phosphate and electrolyte excretion by the kidney, although the physiological significance of this is not reported. Calcitonin has been used clinically for treatment of disorders of calcium metabolism and pain, and its relationship to increased glucose levels in mammals has been the subject of varying reports. See, e.g., Azria et al., "Calcitonins—Physiological and Pharmacological Aspects," pp. 24–25 (Springer-Verlag 1989). The use of calcitonins in the treatment of diabetes mellitus is described in U.S. Pat. No. 5,321,008, issued Jun. 14, 1994, and in U.S. Pat. No. 5,508,260, issued Apr. 16, 1996. Certain compounds reported to be calcitonin derivatives have been said to lower the calcium plasma level and to influence bone metabolism in U.S. Pat. No. 4,758,550, issued Jul. 19, 1988.

SUMMARY OF THE INVENTION

The present invention provides novel compounds for use in regulating certain metabolic effects mediated by amylin and calcitonin in mammals. Surprisingly, these compounds act as amylin agonists for certain of amylin's effects and as calcitonin agonists for certain of calcitonin's effects.

Among other factors, the present invention is based on our unexpected discovery that the compounds of the present invention exhibit a biological profile which includes acting as agonists for certain of the effects of calcitonin and amylin. In particular these compounds act as amylin agonists in the inhibition of gastric emptying. Due to their surprising combination of biological effects, these compounds will be useful in treating diabetes, including Type I diabetes and insulin dependent (late stage) Type II diabetes, due in part to their effects on inhibiting gastric emptying. Applicants note that the compounds of the present invention exhibit advantageous biological activity and yet are peptide amides which are less than about half to about two-fifths the size of amylin. Due to their smaller size and molecular weight, these compounds are easier and more economical to synthesize. In addition, these compounds will be more amenable to drug delivery via patch technology, microsphere technology and/or buccal technology, among others. Applicants note that previously reported agonists of amylin were substantially full length. See, e.g., U.S. Pat. No. 5,686,411.

According to the present invention, provided are compounds of the formula I:

$X_1$-$Xaa_1$-$X_2$-$Xaa_2$-$X_3$-$Xaa_3$-$X_4$-$Xaa_4$-$X_5$-$Xaa_5$-$X_6$-$NH_2$
wherein $X_1$ is Lys, Arg or absent;

$X_2$ is $Xaa_6Xaa_7Xaa_8Xaa_9$ (SEQ. ID. NO. 47) or Z-$Xaa_{10}$SerThr, provided that if $X_2$ is Z-$Xaa_{10}$Ser-Thr, then $X_1$ and $Xaa_1$ are both absent;

$X_3$ is AlaThr, AlaSer, SerMet, GluThr or ValThr;

$X_4$ is ArgLeuAla, HisLeuAla, ArgIleAla, LysIleAla, ArgMetAla, HisMetAla, LysMetAla or ArgLeuThr;

$X_5$ is PheLeu, PheIle, PheMet, TyrLeu, TyrIle, TyrMet, TrpMet, TrpIle or TrpMet;

$X_6$ is ArgSerSerGlyTyr (SEQ. ID. NO. 48), LysSerSerGlyTyr (SEQ. ID. NO. 49), HisSerSerGlyTyr (SEQ. ID.

NO. 50), ProSerSerGlyTyr (SEQ. ID. NO. 51), Arg-SerArgGlyTyr (SEQ. ID. NO. 52), ArgThrSerGlyTyr (SEQ. ID. NO. 53), ArgAlaSerGlyTyr (SEQ. ID. NO. 54), AlaSerSerGlyTyr (SEQ. ID. NO. 55), ArgSerAlaGlyTyr (SEQ. ID. NO. 56), HisSerAlaGlyTyr (SEQ. ID. NO. 57), ArgSerGlyTyr (SEQ. ID. NO. 58), ArgSer, LysSer, HisSer, ArgThr, ProSer or Arg;

Xaa$_1$ is Cys or absent;

Xaa$_2$ is Cys or Ala;

Xaa$_3$ is Gln, Ala or Asn;

Xaa$_4$ is Asn, Ala or Gln;

Xaa$_5$ is Val, Ala, Ile, Met, Leu, PentylGly, or t-butylGly;

Xaa$_6$ is Asn, Gln or Asp;

Xaa$_7$ is Thr, Ser, Met, Val, Leu or Ile;

Xaa$_8$ is Ala or Val;

Xaa$_9$ is Thr or Ser;

Xaa$_{10}$ is Leu, Val, Met or Ile; and

Z is an alkanoyl group of about 1 to about 8 carbon atoms or absent;

and pharmaceutically acceptable salts thereof. Methods of using compounds of the present invention in the treatment of various conditions which would benefit such conditions, such as diabetes and gastrointestinal disorders, as well as pharmaceutical compositions containing compounds of the present invention, are also described and claimed herein.

Definitions

In accordance with the present invention and as used herein, the following terms are defined to have the following meanings, unless explicitly stated otherwise.

The term "amylin" is understood to include the human peptide hormone amylin secreted from the beta cells of the pancreas.

"Amylin agonist" is also a term known in the art, and refers to a compound which has one or more biological activities of amylin. An amylin agonist may be a peptide or a non-peptide compound. Such compounds may act as amylin agonists, normally, it is presently believed, by virtue of binding to or otherwise interacting directly or indirectly interacting with an amylin receptor or other receptor or receptors with which amylin itself may interact to elicit a biological response.

The term "amylin antagonist" refers to a compound which inhibits one or more effects of amylin. An amylin antagonist may be a peptide or non-peptide compound.

The term "alkanoyl" refers to the group RC(=O)— wherein R is a straight chain or branched chain alkyl group, which may be derived from a corresponding carboxylic acid.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH— or —NH—R—C(O)— wherein R typically is —CH(R')—, wherein R' is an amino acid side chain, typically H or a carbon containing substitutent; or (2),

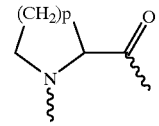

wherein p is 1, 2 or 3 representing the azetidinecarboxylic acid, proline or pipecolic acid residues, respectively. "Calcitonin agonist" refers to a compound which has one or more biological activities of calcitonin. A calcitonin agonist may be a peptide or non-peptide compound.

The term "lower" referred to herein in connection with organic radicals such as alkyl groups defines such groups with up to and including about 6, preferably up to and including 4 and advantageously one or two carbon atoms. Such groups may be straight chain or branched chain. "Pharmaceutically acceptable salt" includes salts of the compounds described herein derived from the combination of such compounds and an organic or inorganic acid. In practice the use of the salt form amounts to use of the base form. The compounds are useful in both free base and salt form.

In addition, the following abbreviations stand for the following:

"ACN" or "CH$_3$CN" refers to acetonitrile.

"Boc", "tBoc" or "Tboc" refers to t-butoxy carbonyl.

"DCC" refers to N,N'-dicyclohexylcarbodiimide.

"Fmoc" refers to fluorenylmethoxycarbonyl.

"HBTU" refers to 2-(1H-benzotriazol-1-yl)-1,1,3,3,-tetramethyluronium hexaflurophosphate.

"HOBt" refers to 1-hydroxybenzotriazole monohydrate.

"homoP" or hPro" refers to homoproline.

"MeAla" or "Nme" refers to N-methylalanine.

"naph" refers to naphthylalanine.

"Pg" or pGly" refers to pentylglycine.

"tBuG" refers to tertiary-butylglycine.

"ThioP" or tPro" refers to thioproline.

3Hyp" refers to 3-hydroxyproline

4Hyp" refers to 4-hydroxyproline

NAG" refers to N-alkylglycine

NAPG" refers to N-alkylpentylglycine

"Norval" refers to norvaline

"Norleu" refers to norleucine

DETAILED DESCRIPTION OF THE INVENTION

Preferred Compounds

According to the present invention, provided are compounds of formula I:

X$_1$-Xaa$_1$-X$_2$-Xaa$_2$-X$_3$-Xaa$_3$-X$_4$-Xaa$_4$-X$_5$-Xaa$_5$-X$_6$-NH$_2$ wherein X$_1$ is Lys, Arg or absent;

X$_2$ is Xaa$_6$Xaa$_7$Xaa$_8$Xaa$_9$ (SEQ. ID. NO. 47) or Z-Xaa$_{10}$SerThr, provided that if X$_2$ is Z-Xaa$_{10}$Ser-Thr, then X$_1$ and Xaa$_1$ are both absent;

X$_3$ is AlaThr, AlaSer, SerMet, GluThr or ValThr;

X$_4$ is ArgLeuAla, HisLeuAla, ArgIleAla, LysIleAla, ArgMetAla, HisMetAla, LysMetAla or ArgLeuThr;

X$_5$ is PheLeu, PheIle, PheMet, TyrLeu, TyrIle, TyrMet, TrpMet, TrpIle or TrpMet;

X$_6$ is ArgSerSerGlyTyr (SEQ. ID. NO. 48), LysSerSerGlyTyr (SEQ. ID. NO. 49), HisSerSerGlyTyr (SEQ. ID. NO. 50), ProSerSerGlyTyr (SEQ. ID. NO. 51), ArgSerArgGlyTyr (SEQ. ID. NO. 52), ArgThrSerGlyTyr (SEQ. ID. NO. 53), ArgAlaSerGlyTyr (SEQ. ID. NO. 54), AlaSerSerGlyTyr (SEQ. ID. NO. 55), ArgSerAlaGlyTyr (SEQ. ID. NO. 56), HisSerAlaGlyTyr (SEQ. ID. NO. 57), ArgSerGlyTyr (SEQ. ID. NO. 58), ArgSer, LysSer, HisSer, ArgThr, ProSer or Arg; and Xaa$_1$ is Cys or absent;

Xaa$_2$ is Cys or Ala;

Xaa$_3$ is Gln, Ala or Asn;

Xaa$_4$ is Asn, Ala or Gln;

Xaa$_5$ is Val, Ala, Ile, Met, Leu, PentylGly, or t-butylGly;

Xaa$_6$ is Asn, Gln or Asp;

Xaa$_7$ is Thr, Ser, Met, Val, Leu or Ile;

Xaa$_8$ is Ala or Val;

Xaa$_9$ is Thr or Ser;

Xaa$_{10}$ is Leu, Val, Met or Ile; and

Z is an alkanoyl group of about 1 to about 8 carbon atoms or absent;

and pharmaceutically acceptable salts thereof.

Preferred are compounds wherein X$_1$ is Lys or absent.

Preferred X$_2$ groups include Xaa$_6$Xaa$_7$Xaa$_8$Xaa$_9$ wherein Xaa$_6$ is Asn, Xaa$_8$ is Ala, and Xaa$_9$ is Thr or Z-Xaa$_{10}$SerThr wherein Xaa$_{10}$ is Leu, Val or Met. When X$_2$ is Xaa$_6$Xaa$_7$Xaa$_8$Xaa$_9$, preferred X$_2$ groups include AsnThrAlaThr (SEQ. ID. NO. 59), AsnValAlaThr (SEQ. ID. NO. 60), AsnLeuAlaThr (SEQ.ID. NO. 61) and AsnMetAlaThr (SEQ. ID. NO. 62). When X$_2$ is Z-Xaa$_{10}$SerThr, especially preferred are compounds wherein Xaa$_{10}$ is Leu.

Preferred X$_3$ groups include AlaThr.

Preferred X$_4$ groups include ArgLeuAla.

Preferred X$_5$ groups include PheLeu.

Preferred X$_6$ groups include ArgSerSerGlyTyr (SEQ. ID. NO. 48), HisSerSerGlyTyr (SEQ. ID. NO. 50), ArgSer and HisSer. Especially preferred are ArgSerSerGlyTyr (SEQ. ID. NO. 48) and ArgSer.

Preferred are compounds wherein Xaa$_3$ is Gln or Ala.

Preferred are compounds wherein Xaa$_4$ is Asn or Ala.

Preferred are compounds wherein Xaa$_5$ is Val or Ala.

Preferred Z groups include alkanoyl groups having about 3 to about 6 carbon atoms.

Preferred compounds include those where Xaa$_1$ and Xaa$_2$ are Cys. According to an especially preferred aspect, the two cysteines may advantageously form a disulfide bridge.

According to one preferred aspect, preferred compounds include those compounds wherein Xaa$_3$ is Ala. Particularly preferred are compounds wherein Xaa$_4$ and Xaa$_5$ are Ala. Alternatively, particularly preferred compounds include compounds wherein Xaa$_4$ is Asn and Xaa$_5$ is Val.

Preferred compounds according to an alternately preferred aspect include compounds wherein Xaa$_3$ is Gln, Xaa$_4$ is Asn and Xaa$_5$ is Val.

According to an alternate aspect, compounds are provided wherein X$_3$ is AlaThr, X$_4$ is ArgLeuAla and X$_5$ is PheLeu. Particularly preferred are compounds wherein X$_6$ is ArgSerSerGlyTyr (SEQ. ID. NO. 48), HisSerSerGlyTyr (SEQ. ID. NO. 60), ArgSer OR HisSer. According to one especially preferred aspect, X$_6$ is ArgSerSerGlyTyr (SEQ. ID. NO. 48) or ArgSer. According to an alternately preferred aspect, X$_6$ is ArgSerSerGlyTyr (SEQ. ID. NO. 48) or HisSerSerGlyTyr (SEQ. ID. NO. 50). Preferred compounds include those wherein Xaa$_1$ is Cys and especially preferred compounds include those wherein Xaa$_2$ is Cys. Where Xaa$_1$ and Xaa$_2$ are both Cys, they may advantageously form a disulfide bridge. Preferably X$_2$ is AsnThrAlaThr (SEQ. ID. NO. 59), AsnValAlaThr (SEQ. ID. NO. 60), AsnLeuAlaThr (SEQ. ID. NO. 61), or AsnMetAlaThr (SEQ. ID. NO. 62). Preferred are compounds wherein Xaa$_3$ is Ala or Glu, wherein Xaa$_4$ is Ala or Asn and wherein Xaa$_5$ is Ala or Val. According to this aspect, especially preferred compounds include those wherein X$_2$ is AsnThrAlaThr (SEQ. ID. NO. 59) or AsnValAlaThr (SEQ. ID. NO. 60), and X$_6$ is ArgSerSerGlyTyr (SEQ. ID. NO. 48). Particularly preferred compounds according to this aspect include those wherein X$_2$ is AsnThrAlaThr (SEQ. ID. NO. 59) and Xaa$_3$, Xaa$_4$, and Xaa$_5$ are Ala; especially preferred are those compounds wherein X$_1$ is Lys. Alternately, particularly preferred compounds according to this aspect include compounds wherein X$_6$ is ArgSer or HisSer, more preferably ArgSer; preferably X$_2$ is AsnValAlaThr (SEQ. ID. NO. 60), Xaa$_3$ is Gln, Xaa$_4$ is Asn, Xaa$_5$ is Val and X$_1$ is absent.

According to an alternate aspect, preferred compounds include those wherein X$_1$ is absent. Especially preferred are compounds wherein Xaa$_1$ is absent. According to this aspect, preferred X$_6$ groups include ArgSer and HisSer, more preferably ArgSer. Particularly preferred compounds according to this aspect include those wherein X$_2$ is Z-Xaa$_{10}$SerThr, preferably Xaa$_{10}$ is Leu, Val or Met. Preferred compounds include those where Xaa$_3$ is Ala, Xaa$_4$ is Ala and Xaa$_5$ is Ala.

Preferred peptide compounds of the present invention include those having an amino acid sequence selected from SEQ. ID. NOS. 1 to 46. Particularly preferred are those having an amino acid sequence selected from SEQ. ID. NOS. 1 to 16. Especially preferred peptide compounds include those having an amino acid sequence selected from SEQ. ID. NOS. 1 to 6.

Also particularly preferred are compounds wherein (a) X$_1$ is Lys or absent and, Xaa$_1$ is Cys and X$_2$ is AsnThrAlaThr (SEQ. ID. NO. 59) or AsnValAlaThr (SEQ. ID. NO. 60) or (b) X$_1$ and Xaa$_1$ are absent and X$_2$ is Z-LeuSerThr. If Xaa$_1$ is absent, then Xaa$_2$ is preferably Ala. If Xaa$_1$ is Cys, then Xaa$_2$ is preferably Cys and Xaa$_1$ and Xaa$_2$ form a disulfide bridge. Especially preferred compounds include those described in Examples 1 to 6 (SEQ. ID. NOS. 1 to 6).

Preparation of Compounds

The compounds described herein may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10 μ, 2.2×25 cm; Vydac, Hesperia, Calif.) may be used to isolate peptides, and purity may be determined using a C4, C8 or C18 analytical column (5 μ, 0.46×25 cm; Vydac). Solvents (A=0.1% TFA/water and B=0.1% TFA/$CH_3CN$) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried out on a VG-Trio machine.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989).

Non-peptide compounds useful in preparing compounds of the present invention may be prepared by art-known methods. For example, phosphate-containing amino acids and peptides containing such amino acids, may be prepared using methods known in the art. See, e.g., Bartlett and Landen, *Biorg. Chem.* 14:356–377 (1986).

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluene-sulfonic acid, maleic acid, fumaric acid succinic acid and tartaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Biological Activity

Activities of the compounds of the present invention are evaluated and/or quantified with various screening assays, including the nucleus accumbens receptor binding assay described in Example A, the C1a agonist assay described in Example B, the C1a binding assay described in Example C and the gastric emptying assay described in Example D.

The nucleus accumbens receptor binding assay, a competition assay which measures the ability of compounds to bind specifically to membrane-bound amylin receptors, is described in U.S. Pat. No. 5,264,372, issued Nov. 23, 1993, the disclosure of which is incorporated herein by reference. The nucleus accumbens receptor binding assay is also described in Example A below. A preferred source of the membrane preparations used in the assay is the basal forebrain which comprises membranes from the nucleus accumbens and surrounding regions. Compounds being assayed compete for binding to these receptor preparations with radiolabeled $^{125}I$ Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson and Rodbard, *Anal. Biochem.* 107:220–239 (1980). The results are reported in Table I.

Peptide compounds of the present invention may be evaluated for agonist activity using the procedures described in Example B. The plasma membrane preparation of a 7-transmembrane-G-protein coupled receptor (GPCR) contains not only the receptor but also the G-proteins which constitute the first step in the intracellular signal transduction process when the receptor is activated by an agonist ligand. These G-proteins have a guanine nucleotide binding site, normally occupied by GDP in the resting or inactive conformation. Agonist activation of a GPCR is accompanied by displacement of GDP by GTP from this site. Thus, measurement of the binding of a radiolabelled ligand, namely [$^{35}$S]-GTPγS, for this binding site constitutes a measure of agonist potency for a given ligand. For agonism at the C1a receptor, a similar membrane preparation to that described below for the C1a binding studies is used. C1a pcDNA construction and transfection were carried out as previously described (Albrandt et al. 1993, FEBS Letters, 325:225–232). HEK293 cell lines showing stable expression of the rat C1a-type calcitonin receptor (C1a/293) or the human C1a-type calcitonin receptor (1154/293) were selected by G418 resistance and limiting dilution culture methods. Plasma membranes were collected from homogenized HEK293 cells and used in the [$^{35}$S]-GTPγS assay. Individual test peptides at concentrations spanning 6 log units starting at around $10^{-5}$M were examined for their ability to bind [$^{35}$S]-GTPγS. Maximum agonist-specific binding was measured in the presence of 1 μM human calcitonin, constitutive binding was measured in the presence of buffer alone. Peptide potencies ($EC_{50}$'s for concentration response curves) were calculated by non-linear regression using Prism™ (version 2.01, GraphPAD Software, San Diego, Calif.). The results are reported in Table I.

Peptide compounds of the present invention may be evaluated for binding to the C1a receptor using the procedures described in Example C. The C1a receptor is the predominant mammalian calcitonin receptor subtype. C1a pcDNA construction and transfection were carried out as previously described (Albrandt et al. 1993, FEBS Letters, 325:225–232). HEK293 cell lines showing stable expression of the rat C1a-type calcitonin receptor (C1a/293) or the human C1a-type calcitonin receptor (1154/293) were selected by G418 resistance and limiting dilution culture methods. Plasma membranes were collected from homogenized HEK293 cells and used in the receptor binding assay. Individual test peptides at concentrations spanning 6 log units starting at around $10^{-6}$M were examined for their ability to displace [$^{125}$I]-human calcitonin from the plasma membrane preparation using a 96-well microtiter plate format and scintillation counting with a Wallac LKB Beta plate counter. Competitive binding curves were constructed. Non-specific binding was measured in the presence of 100 nM calcitonin. Peptide potencies ($IC_{50}$'s for competitive binding) were calculated by non-linear regression using Prism™ (version 2.01, GraphPAD Software, San Diego, Calif.). The results are reported in Table I.

Peptide compounds of the present invention may be evaluated for amylin agonist activity using the methods of measuring the rate of gastric emptying disclosed in, for example, Young et al., *Diabetologia*, 38(6):642–648 (1995). In a phenol red method, which is described in Example D below, conscious rats receive by gavage an a caloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage. The results are reported in Table II.

Preferably, compounds of the present invention exhibit activity in the nucleus accumbens receptor binding assay on the order of less than about 1 to 100 nM, and more preferably less than about 10 nM. In the gastric emptying assays, preferred compounds show $ED_{50}$ values on the order of less than about 100 μg/rat, and more preferably less than about 10 μg/rat.

Formulation and Administration

Compositions useful in the invention may conveniently be provided in the form of formulations suitable for parenteral (including intravenous, intramuscular and subcutaneous) or nasal or oral administration or suitably encapsulated or otherwise prepared by art-known methods for oral administration. A suitable administration format may best be determined by a medical practitioner for each patient individually. Pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

Preferably, these parenteral dosage forms are prepared according to the commonly owned patent applications entitled, "Parenteral, Liquid Formulations for Amylin Agonist Peptides," Ser. No. 60/035,140, filed Jan. 8, 1997, and U.S. application Ser. No. 09/005,262, filed Jan. 8, 1998, which are incorporated herein by this reference, and include approximately 0.01 to 0.5% (w/v), respectively, of a compound in an aqueous system along with approximately 0.02 to 0.5% (w/v) of an acetate, phosphate, citrate or glutamate buffer to obtain a pH of the final composition of approximately 3.0 to 6.0 (more preferably 3.0 to 5.5), as well as approximately 1.0 to 10% (w/v) of a carbohydrate or polyhydric alcohol tonicifier in an aqueous continuous phase. Approximately 0.005 to 1.0% (w/v) of an antimicrobial preservative selected from the group consisting of m-cresol, benzyl alcohol, methyl, ethyl, propyl and butyl parabens and phenol is also present in the preferred formulation of product designed to allow the patient to withdraw multiple doses. A sufficient amount of water for injection is used to obtain the desired concentration of solution. Sodium chloride, as well as other excipients, may also be present, if desired. Such excipients, however, must maintain the overall stability of the peptide. Liquid formulations should be substantially isotonic, that is, within ±20% of isotonicity, and preferably within 10% isotonicity. Most preferably, in the formulation for parenteral administration, the polyhydric alcohol is mannitol, the buffer is an acetate buffer, the preservative is approximately 0.1 to 0.3 w/v % of m-cresol, and the pH is approximately 3.7 to 4.3.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of a compound of the present invention, for example, a compound which will be effective in one or multiple doses to provide a therapeutic effect at the selected level. Therapeutically effective amounts of a compound of the present invention for use in the control of hyperglycemia, including hyperglycemia associated with insulin resistance, are those that significantly lower post-prandial glucose levels with respect to control, as may be measured by comparing the area under the curve of postprandial glucose concentrations. As will be recognized by those in the field, an effective amount of therapeutic agent will vary with many factors including the age and weight of the patient, the patient's physical condition, the action to be obtained and other factors.

The effective single, divided or continuous doses of the compounds will typically be in the range of about 0.1 μg/kg/day to about 1,000 μg/kg/day, preferably about 1.0 μg/kg/day to about 100 μg/kg/day, administered in a single dose or multiple doses.

As will be recognized by those in the field, an effective amount of therapeutic agent will vary with many factors including the age and weight of the patient, the patient's physical condition and other factors. Orally active compounds may be taken orally, however, dosages should be increased 5–10 fold, or should be increased (or decreased) in the ratio described earlier.

To assist in understanding the present invention, the following Examples are included which describe the results of several experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of Mono-disulfide Bridged Amidated Peptide Having the Sequence:
Lys Cys Asn Thr Ala Thr Cys Ala Thr Ala Arg Leu Ala Ala Phe Leu Ala Arg Ser Ser Gly Tyr-NH$_2$ (SEQ. ID. NO. 1).

The above peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and HATU chemistry (O-(7-azabenzotriazol-1-yl)-1,1,3,3,-tetramethyluronium hexafluorphosphate) in the presence of diisopropylethylamine using N-methyl pyrrolidine as solvent was employed. However, at some positions coupling was less efficient than expected and double couplings were required. Deprotection (Fmoc group removal) of the growing peptide chain was achieved using piperidine. The N-terminus was completed using (bis-tBoc)-Lysine in the final coupling cycle. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized and the resulting crude peptide was redissolved in water and treated briefly with tris-carboethoxy phosphine to ensure complete generation of free thiols. Exposure to potassium ferricyanide at pH 6.5 effected cyclization to the mono-disulfide bridged peptide. Acidification and treatment with Biorad AG4X4 anion exchange resin removed any residual $Fe^{2+}$ and $Fe^{3+}$ ions. Lyophilisation gave the crude peptide. Crude purity was about 75%.

Used in purification steps and analysis were Solvent A (0.1% TFA in water) and Solvent B (0.1% TFA in $CH_3CN$).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 5% to 95% Solvent B in Solvent A over 30 minutes) of the lyophilized peptide gave product peptide having an observed retention time of 12.96 minutes. Electrospray Mass Spectrometry (M): calculated 2272.12; found 2273.76 (M+H).

Example 2

Preparation of Mono-disulfide Bridged Amidated Peptide Having the Sequence:
Lys Cys Asn Val Ala Thr Cys Ala Thr Gln Arg Leu Ala Asn Phe Leu Val Arg Ser Ser Gly Tyr-NH$_2$ (SEQ. ID. NO. 2).

The above peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in $CH_3CN$). Analytical RP-HPLC (gradient 20% to 60% Solvent B in Solvent A over 30 minutes) of the lyophilized peptide gave product peptide having an observed retention time of 18.48 minutes. Electrospray Mass Spectrometry (M): calculated 2398.2; found 2399.9 (M+H).

Example 3
Preparation of Mono-disulfide Bridged Amidated Peptide Having the Sequence:
Cys Asn Thr Ala Thr Cys Ala Thr Ala Arg Leu Ala Ala Phe Leu Ala Arg Ser-NH$_2$ (SEQ. ID. NO. 3).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence was completed after addition of the second protected cysteine residue. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 16.93 minutes. Electrospray Mass Spectrometry (M): calculated 1836.91; found 1838.9 (M+H).

Example 4
Preparation of Amidated Peptide Having the Sequence:
isocaproyl-Leu Ser Thr Ala Ala Thr Ala Arg Leu Ala Ala Phe Leu Ala Arg Ser-NH$_2$ (SEQ. ID. NO. 4).

The above peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and HATU chemistry (O-(7-azabenzotriazol-1-yl)-1,1,3,3,-tetramethyluronium hexafluorphosphate) in the presence of diisopropylethylamine using N-methyl pyrrolidine as solvent was employed. However, at some positions coupling was less efficient than expected and double couplings were required. Deprotection (Fmoc group removal) of the growing peptide chain was achieved using piperidine. The N-terminus was completed using isocaproyl-Leucine in the final coupling cycle. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.). The peptide was precipitated in ether/water (50 mL) and centrifuged. The precipitate was reconstituted in glacial acetic acid and lyophilized and the resulting crude peptide was redissolved in water. Lyophilisation gave the crude peptide. Crude purity was about 75%.

Used in purification steps and analysis were Solvent A (0.1% TFA in water) and Solvent B (0.1% TFA in CH$_3$CN). The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 20% to 50% Solvent B in Solvent A over 30 minutes) of the lyophilized peptide gave product peptide having an observed retention time of 29.17 minutes. Electrospray Mass Spectrometry (M): calculated 1716.00; found 1716.85 (M+H).

Example 5
Preparation of Mono-disulfide Bridged Amidated Peptide Having the Sequence:
Lys Cys Asn Thr Ala Thr Cys Ala Thr Ala Arg Leu Ala Asn Phe Leu Ala Val Arg Ser Ser Gly Tyr-NH$_2$ (SEQ. ID. NO. 5).

The above peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 20.57 minutes. Electrospray Mass Spectrometry (M): calculated 2343.16; found 2344.24 (M+H).

Example 6
Preparation of Amidated Peptide Having the Sequence:
Leu Ser Thr Ala Ala Thr Ala Arg Leu Ala Ala Phe Leu Ala Arg Ser-NH$_2$ (SEQ. ID. NO. 6).

The above peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and HATU chemistry (O-(7-azabenzotriazol-1-yl)-1,1,3,3,-tetramethyluronium hexafluorphosphate) in the presence of diisopropylethylamine using N-methyl pyrrolidine as solvent was employed. However, at some positions coupling was less efficient than expected and double couplings were required. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.). The peptide was precipitated in ether/water (50 mL) and centrifuged. The precipitate was reconstituted in glacial acetic acid and lyophilized and the resulting crude peptide was redissolved in water. Lyophilisation gave the crude peptide. Crude purity was about 75%.

Used in purification steps and analysis were Solvent A (0.1% TFA in water) and Solvent B (0.1% TFA in CH$_3$CN). The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 50% Solvent B in Solvent A over 30 minutes) of the lyophilized peptide gave product peptide having an observed retention time of 16.96 minutes. Electrospray Mass Spectrometry (M): calculated 1617.93; found 1618.73 (M+H).

Example 7
Preparation of Mono-disulfide Bridged Amidated Peptide Having the Sequence:
Cys Asn Thr Ala Thr Cys Ala Thr Ala Arg Leu Ala Ala Phe Leu Ala Arg-NH$_2$ (SEQ. ID. NO. 7).

The above peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence was completed after addition of the second protected cysteine residue. Used in analysis were Solvent A (0.1% TFA in water) and Solvent B (0.1% TFA in CH$_3$CN). Analytical RP-HPLC (gradient 35% to 65% Solvent B in Solvent A over 30 minutes) of the lyophilized peptide gave product peptide having an observed retention time of 8.63 minutes.

Example 8
Preparation of Mono-disulfide Bridged Amidated Peptide Having the Sequence:
Lys Cys Asn Thr Ala Thr Cys Ala Thr Gln Arg Leu Ala Ala Phe Leu Val Arg Ser Ser Gly Tyr-NH$_2$ (SEQ. ID. NO. 8).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 20.76 minutes. Electrospray Mass Spectrometry (M): calculated 2357.17; found 2357.6 (M+H).

Example 9
Preparation of Mono-disulfide Bridged Amidated Peptide Having the Sequence:
Lys Cys Asn Thr Ala Thr Cys Ala Thr Gln Arg Leu Ala Asn Phe Leu Val Arg Ser Gly Tyr-NH$_2$ (SEQ. ID. NO. 9).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 19.66 minutes. Electrospray Mass Spectrometry (M): calculated 2313.15; found 2314.77 (M+H).

Example 10
Preparation of Mono-disulfide Bridged Amidated Peptide Having the Sequence:
Lys Cys Asn Thr Ala Thr Cys Ala Thr Gln Arg Leu Ala Asn Phe Leu Val Arg Ala Ser Gly Tyr-NH$_2$ (SEQ. ID. NO. 10).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 17.35 minutes. Electrospray Mass Spectrometry (M): calculated 2384.18; found 2385.63 (M+H).

Example 11
Preparation of Mono-disulfide Bridged Amidated Peptide Having the Sequence:
Lys Cys Asn Thr Ala Thr Cys Ala Thr Gln Arg Leu Ala Asn Phe Leu Val His Ser Ser Gly Tyr-NH$_2$ (SEQ. ID. NO. 11).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 21.06 minutes. Electrospray Mass Spectrometry (M): calculated 2381.14; found 2382.30 (M+H)

Example 12
Preparation of Mono-disulfide Bridged Amidated Peptide Having the Sequence:
Lys Cys Asn Thr Ala Thr Cys Ala Thr Gln Arg Leu Ala Asn Phe Leu Val Ala Ser Ser Gly Tyr-NH$_2$ (SEQ. ID. NO. 12).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 16.19 minutes. Electrospray Mass Spectrometry (M): calculated 2315.12; found 2315.94 (M+H).

Example 13
Preparation of Mono-disulfide Bridged Amidated Peptide Having the Sequence:
Cys Asn Thr Ala Thr Cys Ala Thr Gln Arg Leu Ala Asn Phe Leu Val Arg Ser Ser Gly Tyr-NH$_2$ (SEQ. ID. NO. 13).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence was completed after addition of the second protected cysteine residue. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 21.02 minutes. Electrospray Mass Spectrometry (M): calculated 2272.08; found 2272.9 (M+H).

Example 14
Preparation of Mono-disulfide Bridged Amidated Peptide Having the Sequence:
Lys Cys Asn Thr Ala Thr Cys Ala Thr Gln Arg Leu Ala Asn Phe Leu Val Arg Ser Ser Gly Tyr-NH$_2$ (SEQ. ID. NO. 14).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide gave product peptide having an observed retention time of 16.76 minutes. Electrospray Mass Spectrometry (M): calculated 2400.18; found 2400.13.

Example 15
Preparation of Mono-disulfide Bridged Amidated Peptide Having the Sequence:
Lys Cys Asn Thr Ala Thr Cys Ala Thr Gln Arg Leu Ala Asn Phe Leu Val Arg Ser Ala Gly Tyr-NH$_2$ (SEQ. ID. NO. 15).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide gave product peptide having an observed retention time of 18.70 minutes. Electrospray Mass Spectrometry (M): calculated 2384.18; found 2385.04 (M+H).

Example 16
Preparation of Mono-disulfide Bridged Amidated Peptide Having the Sequence:
Lys Cys Asn Thr Ala Thr Cys Ala Thr Gln Arg Leu Ala Asn Phe Leu Ala Arg Ser Ser Gly Tyr-$NH_2$ (SEQ. ID. NO. 16).

The above-identified peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis were Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide gave product peptide having an observed retention time of 18.85 minutes. Electrospray Mass Spectrometry (M): calculated 2372.15; found 2372.97 (M+H).

Example 17
Preparation of Mono-disulfide Bridged Amidated Peptide Having the Sequence:
Lys Cys Asn Val Ala Thr Cys Ala Thr Ala Arg Leu Ala Ala Phe Leu Ala Arg Ser Ser Gly Tyr-$NH_2$ (SEQ. ID. NO. 17).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2270.14.

Example 18
Preparation of Mono-disulfide Bridged Amidated Peptide Having the Sequence:
Lys Cys Asn Val Ala Thr Cys Ala Thr Ala Arg Leu Ala Ala Phe Leu Ala His Ser Ser Gly Tyr-$NH_2$ (SEQ. ID. NO. 18).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2251.10.

Example 19
Preparation of Mono-disulfide Bridged Amidated Peptide Having the Sequence:
Lys Cys Asn Leu Ala Thr Cys Ala Thr Ala Arg Leu Ala Ala Phe Leu Ala Arg Ser Ser Gly Tyr-$NH_2$ (SEQ. ID. NO. 19).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2284.16.

Example 20
Preparation of Mono-disulfide Bridged Amidated Peptide Having the Sequence:
Lys Cys Asn Leu Ala Thr Cys Ala Thr Ala Arg Leu Ala Ala Phe Leu Ala His Ser Ser Gly Tyr-$NH_2$ (SEQ. ID. NO. 20).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2265.11.

Example 21
Preparation of Mono-disulfide Bridged Amidated Peptide Having the Sequence:
Lys Cys Asn Met Ala Thr Cys Ala Thr Ala Arg Leu Ala Ala Phe Leu Ala Arg Ser Ser Gly Tyr-$NH_2$ (SEQ. ID. NO. 21).

The above-identified peptide is assembled on 4-(2'-4'-dimethoxyphenyl)-Fmoc aminomethyl phenoxy acetamide Adnorleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2302.11.

Example 22
Preparation of Mono-disulfide Bridged Amidated Peptide Having the Sequence:
Lys Cys Asn Met Ala Thr Cys Ala Thr Ala Arg Leu Ala Ala Phe Leu Ala His Ser Ser Gly Tyr-$NH_2$ (SEQ. ID. NO. 22).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in $CH_3CN$). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2283.07.

Example 23
Preparation of Mono-disulfide Bridged Amidated Peptide Having the Sequence:
Lys Cys Asn Leu Ala Thr Cys Ala Thr Gln Arg Leu Ala Asn Phe Leu Val Arg Ser Ser Gly Tyr-NH$_2$ (SEQ. ID. NO. 23).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2412.22.

Example 24
Preparation of Mono-disulfide Bridged Amidated Peptide Having the Sequence:
Lys Cys Asn Leu Ala Thr Cys Ala Thr Gln Arg Leu Ala Asn Phe Leu Val His Ser Ser Gly Tyr-NH$_2$ (SEQ. ID. NO. 24).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2393.17.

Example 25
Preparation of Mono-disulfide Bridged Amidated Peptide Having the Sequence:
Lys Cys Asn Val Ala Thr Cys Ala Thr Ala Arg Leu Ala Asn Phe Leu Val Arg Ser Ser Gly Tyr-NH$_2$ (SEQ. ID. NO. 25).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2341.18.

Example 26
Preparation of Mono-disulfide Bridged Amidated Peptide Having the Sequence:
Lys Cys Asn Val Ala Thr Cys Ala Thr Ala Arg Leu Ala Asn Phe Leu Val His Ser Ser Gly Tyr-NH$_2$ (SEQ. ID. NO. 26).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2322.13.

Example 27
Preparation of Mono-disulfide Bridged Amidated Peptide Having the Sequence:
Cys Asn Val Ala Thr Cys Ala Thr Ala Arg Leu Ala Ala Phe Leu Ala Arg Ser Ser Gly Tyr-NH$_2$ (SEQ. ID. NO. 27).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2142.05.

Example 28
Preparation of Mono-disulfide Bridged Amidated Peptide Having the Sequence:
Cys Asn Val Ala Thr Cys Ala Thr Ala Arg Leu Ala Ala Phe Leu Ala His Ser Ser Gly Tyr-NH$_2$ (SEQ. ID. NO. 28).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2123.00.

Example 29
Preparation of Mono-disulfide Bridged Amidated Peptide Having the Sequence:
Cys Asn Leu Ala Thr Cys Ala Thr Ala Arg Leu Ala Ala Phe Leu Ala Arg Ser Ser Gly Tyr-NH$_2$ (SEQ. ID. NO. 29).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2156.06.

Example 30
Preparation of Mono-disulfide Bridged Amidated Peptide Having the Sequence:
Cys Asn Leu Ala Thr Cys Ala Thr Ala Arg Leu Ala Ala Phe Leu Ala His Ser Ser Gly Tyr-NH$_2$ (SEQ. ID. NO. 30).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2137.02.

Example 31
Preparation of Mono-disulfide Bridged Amidated Peptide Having the Sequence:
Cys Asn Met Ala Thr Cys Ala Thr Ala Arg Leu Ala Ala Phe Leu Ala Arg Ser Ser Gly Tyr-NH$_2$ (SEQ. ID. NO. 31).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2174.02.

Example 32
Preparation of Mono-disulfide Bridged Amidated Peptide Having the Sequence:
Cys Asn Met Ala Thr Cys Ala Thr Ala Arg Leu Ala Ala Phe Leu Ala His Ser Ser Gly Tyr-NH$_2$ (SEQ. ID. NO. 32).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2154.98.

Example 33
Preparation of Mono-disulfide Bridged Amidated Peptide Having the Sequence:
Cys Asn Leu Ala Thr Cys Ala Thr Gln Arg Leu Ala Asn Phe Leu Val Arg Ser Ser Gly Tyr-NH$_2$ (SEQ. ID. NO. 33).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2284.12.

Example 34
Preparation of Mono-disulfide Bridged Amidated Peptide Having the Sequence:
Cys Asn Leu Ala Thr Cys Ala Thr Gln Arg Leu Ala Asn Phe Leu Val His Ser Ser Gly Tyr-NH$_2$ (SEQ. ID. NO. 34).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2265.08.

Example 35
Preparation of Mono-disulfide Bridged Amidated Peptide Having the Sequence:
Cys Asn Val Ala Thr Cys Ala Thr Ala Arg Leu Ala Asn Phe Leu Val Arg Ser Ser Gly Tyr-NH$_2$ (SEQ. ID. NO. 35).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2213.08.

Example 36
Preparation of Mono-disulfide Bridged Amidated Peptide Having the Sequence:
Cys Asn Val Ala Thr Cys Ala Thr Ala Arg Leu Ala Asn Phe Leu Val His Ser Ser Gly Tyr-NH$_2$ (SEQ. ID. NO. 36).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected, cyclized and purified in a similar way to Example 1. The sequence is complete after addition of the second protected cysteine residue. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 2194.03.

Example 37
Preparation of Amidated Peptide Having the Sequence: isocaproyl-Leu Ser Thr Ala Ala Thr Ala Arg Leu Ala Ala Phe Leu Ala His Ser-NH$_2$ (SEQ. ID. NO. 37).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. The N-terminus is completed using isocaproyl-Leucine in the final coupling cycle. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1695.96.

Example 38
Preparation of Amidated Peptide Having the Sequence: isocaproyl-Val Ser Thr Ala Ala Thr Ala Arg Leu Ala Ala Phe Leu Ala Arg Ser-NH$_2$ (SEQ. ID. NO. 38).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. The N-terminus is completed using isocaproyl-Valine in the final coupling cycle. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1700.98.

Example 39
Preparation of Amidated Peptide Having the Sequence: isocaproyl-Val Ser Thr Ala Ala Thr Ala Arg Leu Ala Ala Phe Leu Ala His Ser-NH$_2$ (SEQ. ID. NO. 39).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. The N-terminus is completed using isocaproyl-Valine in the final coupling cycle. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1681.94.

Example 40
Preparation of Amidated Peptide Having the Sequence: isocaproyl-Met Ser Thr Ala Ala Thr Ala Arg Leu Ala Ala Phe Leu Ala Arg Ser-NH$_2$ (SEQ. ID. NO. 40).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. The N-terminus is completed using isocaproyl-Methionine in the final coupling cycle. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1732.95.

Example 41
Preparation of Amidated Peptide Having the Sequence: isocaproyl-Met Ser Thr Ala Ala Thr Ala Arg Leu Ala Ala Phe Leu Ala His Ser-NH$_2$ (SEQ. ID. NO. 41).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 4. The N-terminus is completed using isocaproyl-Methionine in the final coupling cycle. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1713.91.

Example 42
Preparation of Amidated Peptide Having the Sequence: Leu Ser Thr Ala Ala Thr Ala Arg Leu Ala Ala Phe Leu Ala His Ser-NH$_2$ (SEQ. ID. NO. 42).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 6. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1598.89.

Example 43
Preparation of Amidated Peptide Having the Sequence: Val Ser Thr Ala Ala Thr Ala Arg Leu Ala Ala Phe Leu Ala Arg Ser-NH$_2$ (SEQ. ID. NO. 43).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 6. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1603.92.

Example 44
Preparation of Amidated Peptide Having the Sequence: Val Ser Thr Ala Ala Thr Ala Arg Leu Ala Ala Phe Leu Ala His Ser-NH$_2$ (SEQ. ID. NO. 44).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 6. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1584.87.

Example 45
Preparation of Amidated Peptide Having the Sequence:
Met Ser Thr Ala Ala Thr Ala Arg Leu Ala Ala Phe Leu Ala Arg Ser-NH$_2$ (SEQ. ID. NO. 45).

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 6. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1635.89.

Example 46
Preparation of Amidated Peptide Having the Sequence:
Met Ser Thr Ala Ala Thr Ala Arg Leu Ala Ala Phe Leu Ala His Ser-NH$_2$ (SEQ. ID. NO. 46)

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 6. Used in analysis are Solvent A (0.1% TFA in water) and Solvent B (0.1% TFA in CH$_3$CN). Analytical RP-HPLC (gradient 20% to 50% Solvent B in Solvent A over 30 minutes) of the lyophilized peptide is then carried out to determine the retention time of the product peptide. Electrospray Mass Spectrometry (M): calculated 1616.85.

Example A
Binding to Rat Nucleus Accumbens Membranes (Amylin Receptors)

Evaluation of the binding of compounds to amylin receptors was carried out as follows. $^{125}$I-BH-rat amylin was purchased from Amersham Corporation (Arlington Heights, Ill.). Specific activities at time of use ranged from 1950 to 2000 Ci/mmol. Unlabeled reference peptides were obtained from BACHEM Inc. (Torrance, Calif.) and Penninsula Laboratories (Belmont, Calif.).

Male Sprague-Dawley rats (200 to 250 grams) were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12 to 16 pM in 20 mM HEPES buffer containing 0.5 mg/mL bacitracin, 0.5 mg/mL bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 mL cold PBS, and immediately after filtration with 15 mL cold PBS. Filters were removed and radioactivity assessed in a gamma-counter at a counting efficiency of 77%.

Results, reported as IC$_{50}$'s, are set forth in Table I.

Example B
[$^{35}$S]-GTPγS C1a Agonist Studies

Evaluation of the agonist activity of compounds versus the C1a receptor was carried out as follows:

Reference peptides used in these studies were purchased from Bachem (Torrance, Calif.). All other chemicals were of the highest commercial grade. [$^{35}$S]-GTPγS was purchased from NEN Life Science Products, Inc., Pittsburgh, Pa. [$^{125}$I]-human calcitonin was purchased from Amersham Pharmacia Biotech, Inc., Piscataway, N.J.

Methods for C1a pcDNA construction and transfection have been previously described (Albrandt, et al. 1993, FEBS Letters, 325:225–232). HEK293 cell lines stably expressing the rat C1a-type calcitonin receptor (C1a/293) or the human C1a-type calcitonin receptor (1154/293) were selected by G418 resistance and limiting dilution culture methods.

Confluent cells were detached from tissue culture flasks by incubation with 5 mM EDTA in PBS. Cells were homogenized in ice-cold 20 mM HEPES, pH 7.4 with a Polytron homogenizer. Plasma membranes were collected using three cycles of washing in fresh buffer followed by centrifugation for 15 minutes at 48,000×g. The final membrane pellet was resuspended in 20 mM HEPES buffer containing 0.2 mM phenylmethylsulfonyl fluoride (PMSF) and stored at −70° C.

Assay buffer contained 1 μM GDP, 1 mM EDTA, 5 mM MgCl$_2$, 20 mM Hepes, and 150 mM NaCl, pH 7.4. Membranes (7.5 μg membrane protein/well), [$^{35}$S]-GTPγS (200 pM), and peptides were combined in 200 μL buffer in 96-well microtiter plates. After a 75 minute incubation at room temperature, well contents were harvested onto GF/B glass fiber pads using a Tomtec Mach II plate harvestor (Hamden, Conn.). Dried pads were combined with scintillant and counted on a Wallac LKB Beta Plate scintillation counter. For concentration response curves, samples were run in duplicate over a 6 log concentration range starting at 10$^{-6}$ M or 10$^{-7}$ M. Maximum agonist-specific binding was measured in the presence of 1 μM human calcitonin, constitutive binding was measured in the presence of buffer alone.

Peptide potencies (1C$_{50}$'s for competitive binding, and EC$_{50}$'s for concentration response curves) were calculated by non-linear regression using Prism (version 2.01, Graph-PAD Software, San Diego, Calif.).

Results, reported as ED$_{50}$'s, are set forth in Table I.

Example C
C1a/293 Competitive Binding Studies:

Compounds were evaluated for competition in binding to the C1a receptor as follows:

Reference peptides used in these studies were purchased from Bachem (Torrance, Calif.). All other chemicals were of the highest commercial grade. [$^{35}$S]-GTPγS was purchased from NEN Life Science Products, Inc., Pittsburgh, Pa. [$^{125}$I]-human calcitonin was purchased from Amersham Pharmacia Biotech, Inc., Piscataway, N.J.

Methods for C1a pcDNA construction and transfection have been previously described (Albrandt, et al. 1993). HEK293 cell lines stably expressing the rat C1a-type calcitonin receptor (C1a/293) or the human C1a-type calcitonin receptor (1154/293) were selected by G418 resistance and limiting dilution culture methods.

Confluent cells were detached from tissue culture flasks by incubation with 5 mM EDTA in PBS. Cells were homogenized in ice-cold 20 mM HEPES, pH 7.4 with a Polytron homogenizer. Plasma membranes were collected using three cycles of washing in fresh buffer followed by centrifugation for 15 minutes at 48,000×g. The final membrane pellet was resuspended in 20 mM HEPES buffer containing 0.2 mM phenylmethylsulfonyl fluoride (PMSF) and stored at −70° C.

Assay buffer contained 5 µg/mL bestatin, 1 µg/mL phosphoramidon, 1 mg/mL bovine serum albumin (fraction V), 1 mg/mL bacitracin, 1 mM $MgCl_2$, and 20 mM HEPES, pH 7.4. Membranes (2–5 µg membrane protein/well), [$^{125}$I]-human calcitonin (20 pM), and peptides were combined in 200 µL buffer in 96-well microtiter plates. After a 60 minute incubation at room temperature, well contents were harvested onto polyethyleneimine-treated GF/B glass fiber pads using a Tomtec Mach II plate harvestor (Hamden, Conn.). Dried pads were combined with scintillant and counted on a Wallac LKB Beta Plate scintillation counter (Gaithersburg, Md.). For competitive binding curves, samples were run in duplicate over a 6 log concentration range starting at $10^{-6}$ or $10^{-7}$ M. Non-specific binding was measured in the presence of 100 nM human calcitonin.

Results, reported as $IC_{50}$'s, are set forth in Table I.

TABLE I

| Example No. | SEQ. ID. NO. | $IC_{50}$ (nM) Example A (rAmy) | $IC_{50}$ (nM) Example C (C1a) | $ED_{50}$ (nM) Example B (C1a GTPγS) |
|---|---|---|---|---|
| 1 | 1 | 1.9 | 0.093 | 0.7 |
| 2 | 2 | 44.3 | 0.128 | 2.6 |
| 3 | 3 | 5.7 | 0.190 | 1.2 |
| 4 | 4 | 32 | 0.66 | 0.73 |
| 5 | 5 | 14 | 1.4 | 5.5 |
| 6 | 6 | 78 | 1.4 | 0.58 |
| 7 | 7 | 31 | 2.7 | 2.2 |
| 8 | 8 | 101 | 3.4 | 4.4 |
| 9 | 9 | 91 | 4.1 | 8.6 |
| 10 | 10 | 68 | 4.7 | 8 |
| 11 | 11 | 148 | 8.3 | 14 |
| 12 | 12 | 286 | 10 | 8 |
| 13 | 13 | 95 | 12 | 19 |
| 14 | 14 | 132 | 18 | 90 |
| 15 | 15 | 206 | 18 | 21 |
| 16 | 16 | 31 | 20 | 1.4 |

Example D
Phenol Red Gastric Emptying Assay:

Gastric emptying was measured using a modification (Plourde et al., Life Sci. 53:857–862 (1993)) of the original method of Scarpignato et al. (Arch. Int. Pharmacodyn. Ther. 246:286–295 (1980)). Conscious rats received by gavage. 1.5 mL of an a caloric gel containing 1.5% methyl cellulose (M-0262, Sigma Chemical Co., St. Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to phenol red was derived as the difference between that present in alkaline versus acidified dilutent.

In separate experiments on 7 rats, the stomach and small intestine were both excised and opened into an alkaline solution. The quantity of phenol red that could be recovered from the upper gastrointestinal tract within 29 minutes of gavage was 89±4%; dye which appeared to bind irrecoverably to the gut luminal surface may have accounted for the balance. To compensate for this small loss, percent of stomach contents remaining after 20 minutes were expressed as a fraction of the gastric contents recovered from control rats sacrificed immediately after gavage in the same experiment. Percent gastric emptying contents remaining= (absorbance at 20 min)/(absorbance at 0 min). For those compounds for which $ED_{50}$ data is presented, dose response curves for gastric emptying were fitted to a 4-parameter logistic model using a least-squares iterative routine (ALLFIT, v2.7, NIH, Bethesda, Md.) to derive $ED_{50}$s. Because $ED_{50}$ is log-normally distributed, it is expressed ± standard error of the logarithm. Pairwise comparisons were performed using one-way analysis of variance and the Student-Newman-Keuls multiple comparisons test (Instat v2.0, GraphPad Software, San Diego, Calif.) using P<0.05 as the level of significance.

As a reference point for dose response studies, rat amylin (Bachem, Torrance, Calif.) dissolved in 0.15M saline, was administered as a 0.1 mL subcutaneous bolus in doses of 0, 0.01, 0.1, 1, 10 or 100 µg 5 minutes before gavage in Harlan Sprague Dawley (non-diabetic) rats fasted 20 hours and diabetic BB rats fasted 6 hours. When subcutaneous amylin injections were given 5 minutes before gavage with phenol red indicator, there was a dose-dependent suppression of gastric emptying (data not shown). Suppression of gastric emptying was complete in normal HSD rats administered 1 µg of amylin, and in diabetic rats administered 10 µg (P=0.22, 0.14). The $ED_{50}$ for inhibition of gastric emptying in normal rats was 0.43 µg (0.60 nmol/kg) ±0.19 log units, and was 2.2 µg (2.3 nmol/kg) ±0.18 log units in diabetic rats.

Amylin (rat or human) and compounds that exhibit amylin-like actions in isolated soleus muscle (including, salmon calcitonin, CGRP, and rat calcitonin) have been observed to dose-dependently inhibit gastric emptying in the present conscious rat model. Adrenomedullin, which has been observed to behave as a CGRP agonist but not as an amylin or calcitonin agonist, does not inhibit gastric emptying at the highest doses (100 µg) used in this model (indicating that inhibition of gastric emptying in this model is unlikely to be mediated by CGRP receptors).

Results are set forth in Table II.

TABLE II

| Example No. | SEQ. ID. NO. | Example D $ED_{50}$ (µg) or % Remaining (100 µg) |
|---|---|---|
| 1 | 1 | * 0.26 |
| 3 | 3 | * 0.45 |
| 5 | 5 | * 9.3 |
| 6 | 6 | * 1.34 |
| 13 | 13 | 69% |
| 14 | 14 | 73% |
| rat amylin | N/A | * 0.26 |

*$ED_{50}$

We claim:

1. A compound of the formula:

$X_1$-Xaa$_1$-$X_2$-Xaa$_2$-$X_3$-Xaa$_3$-$X_4$-Xaa$_4$-$X_5$-Xaa$_5$-$X_6$-NH$_2$
wherein $X_1$ is Lys, Arg or absent;

$X_2$ is Xaa$_6$Xaa$_7$Xaa$_8$Xaa$_9$ (SEQ. ID. NO. 47) or Z-Xaa$_{10}$SerThr, provided that if $X_2$ is Z-Xaa$_{10}$Ser-Thr, then $X_1$ and Xaa$_1$ are both absent;

$X_3$ is AlaThr, AlaSer, SerMet, GluThr or ValThr;

$X_4$ is ArgLeuAla, HisLeuAla, ArgIleAla, LysIleAla, ArgMetAla, HisMetAla, LysMetAla or ArgLeuThr;

$X_5$ is PheLeu, PheIle, PheMet, TyrLeu, TyrIle, TyrMet, TrpMet, TrpIle or TrpMet;

$X_6$ is ArgSerSerGlyTyr (SEQ. ID. NO. 48), LysSerSerGlyTyr (SEQ. ID. NO. 49), HisSerSerGlyTyr (SEQ. ID. NO. 50), ProSerSerGlyTyr (SEQ. ID. NO. 51), ArgSerArgGlyTyr (SEQ. ID. NO. 52), ArgThrSerGlyTyr (SEQ. ID. NO. 53), ArgAlaSerGlyTyr (SEQ. ID. NO. 54), AlaSerSerGlyTyr (SEQ. ID. NO. 55), ArgSerAlaGlyTyr (SEQ. ID. NO. 56), HisSerAlaGlyTyr (SEQ. ID. NO. 57), ArgSerGlyTyr (SEQ. ID. NO. 58), ArgSer, LysSer, HisSer, ArgThr, ProSer or Arg;

Xaa$_1$ is Cys or absent;

Xaa$_2$ is Cys or Ala;

Xaa$_3$ is Gln, Ala or Asn;

Xaa$_4$ is Asn, Ala or Gln;

Xaa$_5$ is Val, Ala, Ile, Met, Leu, PentylGly, or t-butylGly;

Xaa$_6$ is Asn, Gln or Asp;

Xaa$_7$ is Thr, Ser, Met, Val, Leu or Ile;

Xaa$_8$ is Ala or Val;

Xaa$_9$ is Thr or Ser;

Xaa$_{10}$ is Leu, Val, Met or Ile; and

Z is an alkanoyl group of about 1 to about 8 carbon atoms or absent and pharmaceutically acceptable salts thereof.

2. A compound according to claim 1 wherein $X_3$ is AlaThr.

3. A compound according to claim 2 wherein $X_4$ is ArgLeuAla.

4. A compound according to claim 3 wherein $X_5$ is PheLeu.

5. A compound according to claim 4 wherein $X_6$ is ArgSerSerGlyTyr (SEQ. ID. NO. 48), HisSerSerGlyTyr (SEQ. ID. NO. 50), ArgSer or HisSer.

6. A compound according to claim 5 wherein $X_6$ is ArgSerSerGlyTyr (SEQ. ID. NO. 48) or ArgSer.

7. A compound according to claim 5 wherein $X_6$ is ArgSerSerGlyTyr (SEQ. ID. NO. 48) or HisSerSerGlyTyr (SEQ. ID. NO. 50).

8. A compound according to claim 7 wherein Xaa$_1$ is Cys.

9. A compound according to claim 8 wherein Xaa$_2$ is Cys.

10. A compound according to claim 9 wherein Xaa$_1$ and Xaa$_2$ form a disulfide bridge.

11. A compound according to claim 9 wherein $X_2$ is AsnThrAlaThr (SEQ. ID. NO. 59), AsnValAlaThr (SEQ. ID. NO. 60), AsnLeuAlaThr (SEQ. ID. NO. 61), or AsnMetAlaThr (SEQ. ID. NO. 62).

12. A compound according to claim 11 wherein Xaa$_3$ is Ala or Gln.

13. A compound according to claim 12 wherein Xaa$_4$ is Ala or Asn.

14. A compound according to claim 13 wherein $Xaa_5$ is Ala or Val.

15. A compound according to claim 14 wherein $X_2$ is AsnThrAlaThr (SEQ. ID. NO. 59) or AsnValAlaThr (SEQ. ID. NO. 60).

16. A compound according to claim 15 wherein $Xaa_1$ and $Xaa_2$ form a disulfide bridge.

17. A compound according to claim 15 wherein $X_6$ is ArgSerSerGlyTyr (SEQ. ID. NO. 48).

18. A compound according to claim 17 wherein $X_2$ is AsnThrAlaThr (SEQ. ID. NO. 59).

19. A compound according to claim 18 wherein $X_1$ is Lys.

20. A compound according to claim 19 wherein $Xaa_3$ is Ala.

21. A compound according to claim 20 wherein $Xaa_4$ is Ala.

22. A compound according to claim 21 wherein $Xaa_5$ is Ala.

23. A compound according to claim 22 wherein $Xaa_1$ and $Xaa_2$ form a disulfide bridge.

24. A compound according to claim 12 wherein $X_2$ is AsnValAlaThr (SEQ. ID. NO. 60).

25. A compound according to claim 24 wherein $Xaa_3$ is Gln.

26. A compound according to claim 25 wherein $Xaa_4$ is Asn.

27. A compound according to claim 26 wherein $Xaa_5$ is Val.

28. A compound according to claim 27 wherein $X_1$ is absent.

29. A compound according to claim 28 wherein $Xaa_1$ and $Xaa_2$ form a disulfide bridge.

30. A compound according to claim 5 wherein $X_6$ is ArgSer or HisSer.

31. A compound according to claim 30 wherein $Xaa_1$ is Cys.

32. A compound according to claim 31 wherein $Xaa_2$ is Cys.

33. A compound according to claim 32 wherein $Xaa_1$ and $Xaa_2$ form a disulfide bridge.

34. A compound according to claim 32 wherein $X_2$ is AsnThrAlaThr (SEQ. ID. NO. 59) or AsnValAlaThr (SEQ. ID. NO. 60).

35. A compound according to claim 34 wherein $X_6$ is ArgSer.

36. A compound according to claim 35 wherein $X_2$ is AsnThrAlaThr (SEQ. ID. NO. 59).

37. A compound according to claim 36 wherein $Xaa_3$ is Ala.

38. A compound according to claim 37 wherein $Xaa_4$ is Ala.

39. A compound according to claim 38 wherein $Xaa_5$ is Ala.

40. A compound according to claim 39 wherein $Xaa_1$ and $Xaa_2$ form a disulfide bridge.

41. A compound according to claim 5 wherein $X_1$ is absent.

42. A compound according to claim 41 wherein $Xaa_1$ is absent.

43. A compound according to claim 42 wherein $X_6$ is ArgSer or HisSer.

44. A compound according to claim 43 wherein $X_2$ is Z-$Xaa_{10}$SerThr.

45. A compound according to claim 44 wherein $Xaa_{10}$ is Leu Val or Met.

46. A compound according to claim 45 wherein $Xaa_4$ is Ala.

47. A compound according to claim 46 wherein $Xaa_3$ is Ala.

48. A compound according to claim 47 wherein $Xaa_5$ is Ala.

49. A compound according to claim 48 wherein $X_6$ is ArgSer.

50. A compound according to claim 49 wherein $Xaa_{10}$ is Leu.

51. A compound according to claim 1 wherein $X_1$ is absent.

52. A compound according to claim 51 wherein $Xaa_1$ is absent.

53. A compound according to claim 52 wherein $X_2$ is Z-$Xaa_{10}$SerThr.

54. A compound according to claim 1 wherein $X_2$ is $Xaa_6Xaa_7Xaa_8Xaa_9$ (SEQ. ID. NO. 47).

55. A compound according to claim 54 wherein $Xaa_6$ is Asn, $Xaa_8$ is Ala and $Xaa_9$ is Thr.

56. A compound according to claim 1 having an amino acid sequence selected from SEQ. ID. NOS. 1 to 46.

57. A compound according to claim 56 having an amino acid sequence selected from SEQ. ID. NOS. 1 to 16.

58. A compound according to claim 57 having an amino acid sequence selected from SEQ. ID. NOS. 1 to 6.

59. A compound according to claim 1 wherein $Xaa_3$ is Ala or Gln, $Xaa_4$ is Ala or Asn and $Xaa_5$ is Ala or Val.

60. A compound according to claim 59 wherein $Xaa_4$ is Ala.

61. A compound according to claim 60 wherein $Xaa_3$ is Ala.

62. A compound according to claim 61 wherein $Xaa_5$ is Ala.

63. A compound according to claim 59 wherein $Xaa_3$ is Gln.

64. A compound according to claim 63 wherein $Xaa_5$ is Val.

65. A compound according to claim 64 wherein $Xaa_4$ is Asn.

66. A compound according to claim 1 wherein $X_4$ is ArgLeuAla.

67. A compound according to claim 1 wherein $X_5$ is PheLeu.

68. A compound according to claim 1 wherein $X_6$ is ArgSerSerGlyTyr (SEQ. ID. NO. 48), HisSerSerGlyTyr (SEQ. ID. NO. 50), ArgSer or HisSer.

69. A compound according to claim 1 wherein $X_2$ is AsnThrAlaThr (SEQ. ID. NO. 59), AsnValAlaThr (SEQ. ID. NO. 60), AsnLeuAlaThr (SEQ. ID. NO. 61) or AsnMetAlaThr (SEQ. ID. NO. 62).

70. A compound according to claim 69 wherein $X_2$ is AsnThrAlaThr (SEQ. ID. NO. 59) or AsnValAlaThr (SEQ. ID. NO. 60).

71. A compound according to claim 1 wherein $Xaa_1$ is Cys.

72. A compound according to claim 72 wherein $Xaa_2$ is Cys.

73. A compound according to claim 73 wherein $Xaa_1$ and $Xaa_2$ form a disulfide bridge.

74. A compound according to claim 1 wherein $X_2$ is absent.

75. A compound according to claim 74 wherein $Xaa_1$ is absent.

76. A compound according to claim 75 wherein $Xaa_2$ is Ala.

77. A pharmaceutical composition comprising a compound of any one of claims 1, 56, 57 or 58 and a pharmaceutically acceptable carrier.

78. A method of treating diabetes in a subject in need of treatment which comprises administering said subject a therapeutically effective amount of a compound of any one of claims 1, 56, 57, or 58.

79. A method according to claim 78 wherein said diabetes is Type I diabetes.

80. A method according to claim 78 wherein said diabetes is Type II diabetes.

81. A method of beneficially regulating gastrointestinal motility in a subject comprising administering to said subject a therapeutically effective amount of a compound of any one of claims 1, 56, 57, or 58.

82. A method according to claim 81 wherein said beneficial regulation of gastrointestinal motility comprises delaying gastric emptying.

* * * * *

SEQUENCE LISTING

<160> NUMBER OF SEQ ID NOS: 62

<210> SEQ ID NO 1
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 1

Lys Cys Asn Thr Ala Thr Cys Ala Thr Ala Arg Leu Ala Ala Phe Leu
 1               5                  10                  15

Ala Arg Ser Ser Gly Tyr
            20

<210> SEQ ID NO 2
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 2

Lys Cys Asn Val Ala Thr Cys Ala Thr Gln Arg Leu Ala Asn Phe Leu
 1               5                  10                  15

Val Arg Ser Ser Gly Tyr
            20

<210> SEQ ID NO 3
<211> LENGTH: 18
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (18)...(18)
<223> OTHER INFORMATION: amidated Ser (serinamide)

<400> SEQUENCE: 3

Cys Asn Thr Ala Thr Cys Ala Thr Ala Arg Leu Ala Ala Phe Leu Ala
 1               5                  10                  15

Arg Ser

```
<210> SEQ ID NO 4
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: SITE
<222> LOCATION: (1)...(1)
<223> OTHER INFORMATION: Xaa in position 1 is isocaproyl-Leu
<220> FEATURE:
<221> NAME/KEY: AMIDATION
<222> LOCATION: (17)...(17)
<223> OTHER INFORMATION: amidated Ser (serinamide)

<400> SEQUENCE: 4

Xaa Leu Ser Thr Ala Ala Thr Ala Arg Leu Ala Ala Phe Leu Ala Arg
 1               5                  10                  15

Ser

<210> SEQ ID NO 5
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 5

Lys Cys Asn Thr Ala Thr Cys Ala Thr Ala Arg Leu Ala Asn Phe Leu
 1               5                  10                  15

Val Arg Ser Ser Gly Tyr
            20

<210> SEQ ID NO 6
<211> LENGTH: 16
<212> TYPE: PRT
<213> ORGANISM: Artificial Sequence
<220> FEATURE:
<223> OTHER INFORMATION: Synthesized amylin agonist
<220> FEATURE:
<221> NAME/KEY: AMIDATION
<222> LOCATION: (16)...(16)
<223> OTHER INFORMATION: amidated Ser (serinamide)

<400> SEQUENCE: 6

Leu Ser Thr Ala Ala Thr Ala Arg Leu Ala Ala Phe Leu Ala Arg Ser
 1               5                  10                  15

<210> SEQ ID NO 7
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (17)...(17)
```

-continued

```
<223> OTHER INFORMATION: amidated Arg (argininamide)

<400> SEQUENCE: 7

Cys Asn Thr Ala Thr Cys Ala Thr Ala Arg Leu Ala Ala Phe Leu Ala
 1               5                  10                  15

Arg

<210> SEQ ID NO 8
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 8

Lys Cys Asn Thr Ala Thr Cys Ala Thr Gln Arg Leu Ala Ala Phe Leu
 1               5                  10                  15

Val Arg Ser Ser Gly Tyr
            20

<210> SEQ ID NO 9
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 9

Lys Cys Asn Thr Ala Thr Cys Ala Thr Gln Arg Leu Ala Asn Phe Leu
 1               5                  10                  15

Val Arg Ser Gly Tyr
            20

<210> SEQ ID NO 10
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 10

Lys Cys Asn Thr Ala Thr Cys Ala Thr Gln Arg Leu Ala Asn Phe Leu

```
                  1               5              10              15

Val Arg Ala Ser Gly Tyr
               20

<210> SEQ ID NO 11
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 11

Lys Cys Asn Thr Ala Thr Cys Ala Thr Gln Arg Leu Ala Asn Phe Leu
 1               5                  10                  15

Val His Ser Ser Gly Tyr
               20

<210> SEQ ID NO 12
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 12

Lys Cys Asn Thr Ala Thr Cys Ala Thr Gln Arg Leu Ala Asn Phe Leu
 1               5                  10                  15

Val Ala Ser Ser Gly Tyr
               20

<210> SEQ ID NO 13
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 13

Cys Asn Thr Ala Thr Cys Ala Thr Gln Arg Leu Ala Asn Phe Leu Val
 1               5                  10                  15

Arg Ser Ser Gly Tyr
               20
```

```
<210> SEQ ID NO 14
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 14

Lys Cys Asn Thr Ala Thr Cys Ala Thr Gln Arg Leu Ala Asn Phe Leu
 1               5                  10                  15

Val Arg Ser Ser Gly Tyr
            20

<210> SEQ ID NO 15
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 15

Lys Cys Asn Thr Ala Thr Cys Ala Thr Gln Arg Leu Ala Asn Phe Leu
 1               5                  10                  15

Val Arg Ser Ala Gly Tyr
            20

<210> SEQ ID NO 16
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 16

Lys Cys Asn Thr Ala Thr Cys Ala Thr Gln Arg Leu Ala Asn Phe Leu
 1               5                  10                  15

Ala Arg Ser Ser Gly Tyr
            20

<210> SEQ ID NO 17
<211> LENGTH: 22
```

```
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 17

Lys Cys Asn Val Ala Thr Cys Ala Thr Ala Arg Leu Ala Ala Phe Leu
 1               5                  10                  15

Ala Arg Ser Ser Gly Tyr
            20

<210> SEQ ID NO 18
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 18

Lys Cys Asn Val Ala Thr Cys Ala Thr Ala Arg Leu Ala Ala Phe Leu
 1               5                  10                  15

Ala His Ser Ser Gly Tyr
            20

<210> SEQ ID NO 19
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 19

Lys Cys Asn Leu Ala Thr Cys Ala Thr Ala Arg Leu Ala Ala Phe Leu
 1               5                  10                  15

Ala Arg Ser Ser Gly Tyr
            20

<210> SEQ ID NO 20
<211> LENGTH: 22
<212> TYPE: PRT
<213> ORGANISM: Artificial Sequence
<220> FEATURE:
<223> OTHER INFORMATION: Synthesized amylin agonist
```

```
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 20

Lys Cys Asn Leu Ala Thr Cys Ala Thr Ala Arg Leu Ala Ala Phe Leu
1               5                   10                  15

Ala His Ser Ser Gly Tyr
            20

<210> SEQ ID NO 21
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 21

Lys Cys Asn Met Ala Thr Cys Ala Thr Ala Arg Leu Ala Ala Phe Leu
1               5                   10                  15

Ala Arg Ser Ser Gly Tyr
            20

<210> SEQ ID NO 22
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 23

Lys Cys Asn Leu Ala Thr Cys Ala Thr Gln Arg Leu Ala Asn Phe Leu
1               5                   10                  15

Val Arg Ser Ser Gly Tyr
            20

<210> SEQ ID NO 24
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 24

Lys Cys Asn Leu Ala Thr Cys Ala Thr Gln Arg Leu Ala Asn Phe Leu
1               5                   10                  15

Val His Ser Ser Gly Tyr
            20

<210> SEQ ID NO 25
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)
<223> OTHER INFORMATION: amidated Tyr (tyrosinamide)

<400> SEQUENCE: 25

Lys Cys Asn Val Ala Thr Cys Ala Thr Ala Arg Leu Ala Asn Phe Leu
1               5                   10                  15

Val Arg Ser Ser Gly Tyr
            20

<210> SEQ ID NO 26
<211> LENGTH: 22
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (2)...(7)
<223> OTHER INFORMATION: disulfide linkage between amino acid Cys at
      positions 2 and 7.
<220> FEATURE:
<221> NAME/KEY: AMIDATION
<222> LOCATION: (22)...(22)

<223> OTHER INFORMATION: amidated Tyr (tyrosinamide)

<400> SEQUENCE: 26

Lys Cys Asn Val Ala Thr Cys Ala Thr Ala Arg Leu Ala Asn Phe Leu
 1               5                  10                  15

Val His Ser Ser Gly Tyr
            20

<210> SEQ ID NO 27
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 27

Cys Asn Val Ala Thr Cys Ala Thr Ala Arg Leu Ala Ala Phe Leu Ala
 1               5                  10                  15

Arg Ser Ser Gly Tyr
            20

<210> SEQ ID NO 28
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 28

Cys Asn Val Ala Thr Cys Ala Thr Ala Arg Leu Ala Ala Phe Leu Ala
 1               5                  10                  15

His Ser Ser Gly Tyr
            20

<210> SEQ ID NO 29
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 29

```
Cys Asn Leu Ala Thr Cys Ala Thr Ala Arg Leu Ala Ala Phe Leu Ala
1               5                  10                  15

Arg Ser Ser Gly Tyr
            20

<210> SEQ ID NO 30
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 30

Cys Asn Leu Ala Thr Cys Ala Thr Ala Arg Leu Ala Ala Phe Leu Ala
1               5                  10                  15

His Ser Ser Gly Tyr
            20

<210> SEQ ID NO 31
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 31

Cys Asn Met Ala Thr Cys Ala Thr Ala Arg Leu Ala Ala Phe Leu Ala
1               5                  10                  15

Arg Ser Ser Gly Tyr
            20

<210> SEQ ID NO 32
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 32

Cys Asn Met Ala Thr Cys Ala Thr Ala Arg Leu Ala Ala Phe Leu Ala
1               5                  10                  15

His Ser Ser Gly Tyr
```

-continued

```
            20

<210> SEQ ID NO 33
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 33

Cys Asn Leu Ala Thr Cys Ala Thr Gln Arg Leu Ala Asn Phe Leu Val
 1               5                  10                  15

Arg Ser Ser Gly Tyr
            20

<210> SEQ ID NO 34
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 34

Cys Asn Leu Ala Thr Cys Ala Thr Gln Arg Leu Ala Asn Phe Leu Val
 1               5                  10                  15

His Ser Ser Gly Tyr
            20

<210> SEQ ID NO 35
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 35

Cys Asn Val Ala Thr Cys Ala Thr Ala Arg Leu Ala Asn Phe Leu Val
 1               5                  10                  15

Arg Ser Ser Gly Tyr
            20

<210> SEQ ID NO 36
```

```
<211> LENGTH: 21
<212> TYPE: PRT
<213> ORGANISM: Artificial Sequence
<220> FEATURE:
<223> OTHER INFORMATION: Synthesized amylin agonist
<220> FEATURE:
<221> NAME/KEY: DISULFID
<222> LOCATION: (1)...(6)
<223> OTHER INFORMATION: disulfide linkage between amino acid Cys at
      positions 1 and 6.
<220> FEATURE:
<221> NAME/KEY: AMIDATION
<222> LOCATION: (21)...(21)
<223> OTHER INFORMATION: amidated Tyr (tyrosinamide)

<400> SEQUENCE: 36

Cys Asn Val Ala Thr Cys Ala Thr Ala Arg Leu Ala Asn Phe Leu Val
 1               5                  10                  15

His Ser Ser Gly Tyr
             20

<210> SEQ ID NO 37
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: SITE
<222> LOCATION: (1)...(1)
<223> OTHER INFORMATION: Xaa in position 1 stands for isocaproyl-Leu
<220> FEATURE:
<221> NAME/KEY: AMIDATION
<222> LOCATION: (17)...(17)
<223> OTHER INFORMATION: amidated Ser (serinamide)

<400> SEQUENCE: 37

Xaa Leu Ser Thr Ala Ala Thr Ala Arg Leu Ala Ala Phe Leu Ala His
 1               5                  10                  15

Ser

<210> SEQ ID NO 38
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: SITE
<222> LOCATION: (1)...(1)
<223> OTHER INFORMATION: Xaa in position 1 stands for isocaproyl-Val
<220> FEATURE:
<221> NAME/KEY: AMIDATION
<222> LOCATION: (17)...(17)
<223> OTHER INFORMATION: amidated Ser (serinamide)

<400> SEQUENCE: 38

Xaa Val Ser Thr Ala Ala Thr Ala Arg Leu Ala Ala Phe Leu Ala Arg
 1               5                  10                  15

Ser

<210> SEQ ID NO 39
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: SITE
<222> LOCATION: (1)...(1)
```

-continued

```
<223> OTHER INFORMATION: Xaa in position 1 stands for isocaproyl-Val
<220> FEATURE:
<221> NAME/KEY: AMIDATION
<222> LOCATION: (17)...(17)
<223> OTHER INFORMATION: amidated Ser (serinamide)

<400> SEQUENCE: 39

Xaa Val Ser Thr Ala Ala Thr Ala Arg Leu Ala Ala Phe Leu Ala His
 1               5                  10                  15

Ser

<210> SEQ ID NO 40
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: SITE
<222> LOCATION: (1)...(1)
<223> OTHER INFORMATION: Xaa in position 1 stands for isocaproyl-Met
<220> FEATURE:
<221> NAME/KEY: AMIDATION
<222> LOCATION: (17)...(17)
<223> OTHER INFORMATION: amidated Ser (serinamide)

<400> SEQUENCE: 40

Xaa Met Ser Thr Ala Ala Thr Ala Arg Leu Ala Ala Phe Leu Ala Arg
 1               5                  10                  15

Ser

<210> SEQ ID NO 41
<211> LENGTH: 17
<212> TYPE: PRT
<213> ORGANISM: Artificial Sequence
<220> FEATURE:
<223> OTHER INFORMATION: Synthesized amylin agonist
<220> FEATURE:
<221> NAME/KEY: SITE
<222> LOCATION: (1)...(1)
<223> OTHER INFORMATION: Xaa in position 1 stands for isocaproyl-Met
<220> FEATURE:
<221> NAME/KEY: AMIDATION
<222> LOCATION: (17)...(17)
<223> OTHER INFORMATION: amidated Ser (serinamide)

<400> SEQUENCE: 41

Xaa Met Ser Thr Ala Ala Thr Ala Arg Leu Ala Ala Phe Leu Ala His
 1               5                  10                  15

Ser

<210> SEQ ID NO 42
<211> LENGTH: 16
<212> TYPE: PRT
<213> ORGANISM: Artificial Sequence
<220> FEATURE:
<223> OTHER INFORMATION: Synthesized amylin agonist
<220> FEATURE:
<221> NAME/KEY: AMIDATION
<222> LOCATION: (16)...(16)
<223> OTHER INFORMATION: amidated Ser (serinamide)

<400> SEQUENCE: 42

Leu Ser Thr Ala Ala Thr Ala Arg Leu Ala Ala Phe Leu Ala His Ser
 1               5                  10                  15

<210> SEQ ID NO 43
<211> LENGTH: 16
```

```
<212> TYPE: PRT
<213> ORGANISM: Artificial Sequence
<220> FEATURE:
<223> OTHER INFORMATION: Synthesized amylin agonist
<220> FEATURE:
<221> NAME/KEY: AMIDATION
<222> LOCATION: (16)...(16)
<223> OTHER INFORMATION: amidated Ser (serinamide)

<400> SEQUENCE: 43

Val Ser Thr Ala Ala Thr Ala Arg Leu Ala Ala Phe Leu Ala Arg Ser
 1               5                  10                  15

<210> SEQ ID NO 44
<211> LENGTH: 16
<212> TYPE: PRT
<213> ORGANISM: Artificial Sequence
<220> FEATURE:
<223> OTHER INFORMATION: Synthesized amylin agonist
<220> FEATURE:
<221> NAME/KEY: AMIDATION
<222> LOCATION: (16)...(16)
<223> OTHER INFORMATION: amidated Ser (serinamide)

<400> SEQUENCE: 44

Val Ser Thr Ala Ala Thr Ala Arg Leu Ala Ala Phe Leu Ala His Ser
 1               5                  10                  15

<210> SEQ ID NO 45
<211> LENGTH: 16
<212> TYPE: PRT
<213> ORGANISM: Artificial Sequence
<220> FEATURE:
<223> OTHER INFORMATION: Synthesized amylin agonist
<220> FEATURE:
<221> NAME/KEY: AMIDATION
<222> LOCATION: (16)...(16)
<223> OTHER INFORMATION: amidated Ser (serinamide)

<400> SEQUENCE: 45

Met Ser Thr Ala Ala Thr Ala Arg Leu Ala Ala Phe Leu Ala Arg Ser
 1               5                  10                  15

<210> SEQ ID NO 46
<211> LENGTH: 16
<212> TYPE: PRT
<213> ORGANISM: Artificial Sequence
<220> FEATURE:
<223> OTHER INFORMATION: Synthesized amylin agonist
<220> FEATURE:
<221> NAME/KEY: AMIDATION
<222> LOCATION: (16)...(16)
<223> OTHER INFORMATION: amidated Ser (serinamide)

<400> SEQUENCE: 46

Met Ser Thr Ala Ala Thr Ala Arg Leu Ala Ala Phe Leu Ala His Ser
 1               5                  10                  15

<210> SEQ ID NO 47
<211> LENGTH: 4
<212> TYPE: PRT
<213> ORGANISM: Artificial Sequence
<220> FEATURE:
<223> OTHER INFORMATION: Synthesized amino acid
<220> FEATURE:
<221> NAME/KEY: VARIANT
<222> LOCATION: (1)...(4)
<223> OTHER INFORMATION: Xaa in position 1 is Asn, Gln or Asp; Xaa in
      position 2 is Thr, Ser, Met, Val, Leu or Ile; Xaa in position 3 is
      Ala or Val; Xaa in position 4 is Thr or Ser.
```

```
<400> SEQUENCE: 47

Xaa Xaa Xaa Xaa
 1

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide

<400> SEQUENCE: 48

Arg Ser Ser Gly Tyr
 1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

Lys Ser Ser Gly Tyr
 1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

His Ser Ser Gly Tyr
 1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide

<400> SEQUENCE: 51

Pro Ser Ser Gly Tyr
 1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

Arg Ser Arg Gly Tyr
 1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide

<400> SEQUENCE: 53
```

Arg Thr Ser Gly Tyr
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic peptide

<400> SEQUENCE: 54

Arg Ala Ser Gly Tyr
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide

<400> SEQUENCE: 55

Ala Ser Ser Gly Tyr
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic peptide

<400> SEQUENCE: 56

Arg Ser Ala Gly Tyr
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide

<400> SEQUENCE: 57

His Ser Ala Gly Tyr
1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic peptide

<400> SEQUENCE: 58

Arg Ser Gly Tyr
1

<210> SEQ ID NO 59
<211> LENGTH: 4
<212> TYPE: PRT
<213> ORGANISM: Artificial Sequence
<220> FEATURE:
<223> OTHER INFORMATION: Synthetic peptide

<400> SEQUENCE: 59

```
Asn Thr Ala Thr
1

<210> SEQ ID NO 60
<211> LENGTH: 4
<212> TYPE: PRT
<213> ORGANISM: Artificial Sequence
<220> FEATURE:
<223> OTHER INFORMATION: Synthetic peptide

<400> SEQUENCE: 60

Asn Val Ala Thr
1

<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61

Asn Leu Ala Thr
1

<210> SEQ ID NO 62
<211> LENGTH: 4
<212> TYPE: PRT
<213> ORGANISM: Artificial Sequence
<220> FEATURE:
<223> OTHER INFORMATION: Synthetic peptide

<400> SEQUENCE: 62

Asn Met Ala Thr
1
```